United States Patent [19]

Walker

[11] Patent Number: 5,833,741
[45] Date of Patent: Nov. 10, 1998

[54] WATERPROOFING AND PRESERVATIVE COMPOSITONS FOR WOOD

[75] Inventor: Leigh E. Walker, Macungie, Pa.

[73] Assignee: Lonza Inc., Fair Lawn, N.J.

[21] Appl. No.: 783,458

[22] Filed: Jan. 16, 1997

[51] Int. Cl.$^6$ .............................. C09K 3/18; A01N 33/12
[52] U.S. Cl. .................. 106/2; 106/15.05; 106/18.32; 427/297; 427/440; 514/642; 514/643; 514/644
[58] Field of Search .............................. 106/15.05, 18.32, 106/2; 514/642, 643, 644; 427/297, 440

[56] References Cited

U.S. PATENT DOCUMENTS

| | | | |
|---|---|---|---|
| 3,296,145 | 1/1967 | Findlan et al. | 514/311 |
| 3,299,073 | 1/1967 | Wakeman et al. | 106/18.32 |
| 3,361,793 | 1/1968 | Wakeman et al. | 106/18.32 |
| 3,361,794 | 1/1968 | Wakeman et al. | 106/18.32 |
| 3,431,265 | 3/1969 | Wakeman et al. | 106/18.32 |
| 3,435,039 | 3/1969 | Wakeman et al. | 106/18.32 |
| 3,484,523 | 12/1969 | Findlan et al. | 514/231.2 |
| 4,005,193 | 1/1977 | Green et al. | 424/78.35 |
| 4,013,804 | 3/1977 | Gruetzman | 427/477 |
| 4,336,151 | 6/1982 | Like et al. | 510/106 |
| 4,508,568 | 4/1985 | Fox | 106/2 |
| 4,716,060 | 12/1987 | Aksha et al. | 106/2 |
| 4,764,214 | 8/1988 | Marx et al. | 106/18.32 |
| 5,084,096 | 1/1992 | Stovicek | 106/18.32 |
| 5,221,329 | 6/1993 | Tarr | 106/2 |
| 5,399,762 | 3/1995 | Walker | 564/296 |
| 5,438,034 | 8/1995 | Walker | 504/158 |
| 5,468,284 | 11/1995 | Sturm | 106/18.32 |
| 5,523,487 | 6/1996 | Walker | 564/296 |
| 5,536,305 | 7/1996 | Yu | 106/18.32 |
| 5,559,155 | 9/1996 | Walker | 514/642 |

*Primary Examiner*—Anthony Green
*Attorney, Agent, or Firm*—Darby & Darby

[57] ABSTRACT

The present invention provides a waterproofing wood preservative system comprising a waterproofer selected from the group consisting of an alkyl amine oxide, an alkyl acetoacetate, and a waterproofing quaternary ammonium compound and a biocide comprising at least one biocidal quaternary ammonium compound wherein said waterproofing quaternary ammonium compound is a $C_{12}$–$C_{30}$ alkyl or $C_6$–$C_{20}$ aryl-substituted alkyl, $C_{12}$–$C_{30}$ alkyl quaternary ammonium composition and said biocidal quaternary ammonium compound is a $C_8$–$C_{12}$ alkyl or $C_6$–C20 aryl-substituted alkyl, $C_8$–$C_{10}$ alkyl quaternary ammonium composition. Said wood preservative system offers protection against both biological and physical decomposition of wood, as for example, that occurring in long term-weathering.

16 Claims, 9 Drawing Sheets

WATERPROOFING AND PRESERVATIVE COMPOSITONS FOR WOOD

FIELD OF THE INVENTION

This invention relates to waterproofing and wood preservation compositions. Alkyl dimethyl amine oxides, alkyl acetoacetates and quaternary ammonium compositions have been found to provide superior waterproofing protection for wood when used in combination with quaternary ammonium biocide compositions. In particular, these waterproofing and wood preservation compositions resist both biological and physical decomposition of wood, and moreover retain such resistance with long-term weathering.

BACKGROUND OF THE INVENTION

Biological decay of wood results from the action of fungi and related organisms on the wood fiber. Biocides are chemicals added to wood treatments which inhibit the growth of such organisms, thus avoiding biological decay. Quaternary ammonium compounds (quats) have been shown to be highly effective biocides against organisms which commonly decay wood.

Specifically, quats, and particularly didecyldimethylammonium chloride (DDAC)

are commonly used as wood preservatives because they possess resistance properties to fungi and termites, to loss of strength, and to electrical sensitivity similar to those of commonly used acidic copper/chromium/arsenic solution (CCA) or ammoniacal copper and arsenic salt solution preservatives. See *Proc of the Am. Wood Pres. Assoc.,* 80:191–210 (1984).

The second cause of wood deterioration, physical decomposition, is the result of the swelling and shrinking of wood which is alternatively exposed to moisture and dried. This decomposition is avoided by preventing the exposure of the wood to moisture using compositions having water-repelling properties. Wax-based compounds are water-repellents commonly used on wood, but are incompatible with quaternary ammonium compounds. Thus, there is a need in the art to develop a composition which can combine both the superior resistance to biological decay imparted by the quaternary ammonium compounds and an effective water repellant and which does not lose its effectiveness over long time periods.

The present inventors have discoverd a waterproofing composition which comprises esters of fatty acids. In addition, alkyl dimethyl amine oxides, alkyl acetoacetates and some quats have been found to be effective waterproofing compositions.

Combinations of quaternary ammonium and amine oxides have been described in U.S. Patents for use as cleaning compositions. In particular, in two patents, Findlan et al. (U.S. Pat. Nos. 3,296,145 and 3,484,523) describe tertiary amine oxides wherein the alkyl radical comprises 8 to 20 carbon atoms in combination with quats such as alkyl ammonium chlorides for use in a surgical soap. Polymeric quaternary ammonium compounds are combined with antifungal agents in an emulsion in Green et al. (U.S. Pat. No. 4,005,193). Amine oxide is used as an emulsifier. This combination functions to stop fungus growth in water-in-oil emulsions. Further, Like et al. (U.S. Pat. No. 4,336,151) describe non-irritating disinfectants for the eye which comprise quaternary ammonium compounds and stearyl dimethylamine oxide.

Gruetzman (U.S. Pat. No. 4,013,804) describes a method of treating wood to be spray-painted, where the quat compound imparts an electrostatic charge to the treated wood so an effective method of spray painting based on electric attraction can be used. Both water-repellency and biocidal effect are expected features of the treatment; however, the treatment segments are done separately, in sequence, and not with a combined treatment solution, and the water-repellant taught is a wax-based composition. U.S. Pat. No. 4,508,568 (Fox) also describes a treatment of wax and quats, which requires a high percentage of surfactant to keep the wax in solution.

The function of quats as a dispersant in a water-repellant compound to coat airplane windshields is disclosed in Tarr (U.S. Pat. No. 5,221,329). Finally, Rajadhyaksha et al. (U.S. Patent No. 4,716,060) describe amide compounds, and suggest that they can be combined with various biocidal compositions as a waterproofing and preservative agent.

Several combinations of quats with various compounds which can function as waterproofers have been considered. Specifically, a textile softening agent was disclosed which is a combination of amine oxide with a $C_{12}$–$C_{18}$ quat. *Chemical Abstracts* 73:67620c (1970). A hair rinse is taught in *Chemical Abstracts* 104:135850p (1986) which comprises an amine oxide with a quat composition. A combination of a water-insoluble quat with an amine oxide is taught forming an anti-static agent. *Chemical Abstracts* 101:92745b (1984). A herbicide composition comprising octadecyldimethylamine and $C_8C_{10}N(CH_3)_2Cl$ is disclosed in *Chemical Abstracts* 117:126452b and a rain-resistant fungicide is described in *Chemical Abstracts* 112:212470 (1990).

Fabric treatments containing quats which lack biocidal action are disclosed in *Chemical Abstracts* 86:44656 (1977) and 107:79448m (1987). The combination of a quat with boric acid as a wood treatment is disclosed in *Chemical Abstracts* 105:99400b (1986) and *Chemical Abstracts* 105:135813 (1986). *Chemical Abstracts* 107:238052w (1987) teaches the use of a quat in combination with an inorganic salt and a urea-formed resin to produce a wood treatment. Finally, the use of DDAC in detergents and in liposomes for drug delivery is disclosed in *Chemical Abstracts* 120:301698x (1993) and *Chemical Abstracts* 103:3249u (1985), respectively.

Thus, the present inventors are the first to describe an effective combination of quaternary ammonium compounds with the specifically enlisted non-wax waterproofers for use in the treatment of wood to avoid both physical and biological decay. Such chemical combinations have resulted in treatment systems for wood which show good initial decay resistance which is retained to a significant degree for up to 3 years of exposure to outside weathering. This retention is unexpectedly good and better than either traditional non-biocidal wax-based commercial waterproofers or for the waterproofing composition alone.

BRIEF DESCRIPTION OF THE DRAWINGS

The following abbreviations are used throughout the Figures: TWS—Thompson's Water Seal®, a commercial, over-the-counter non-biocidal material (positive control for waterproofing); PGHMS—Propylene glycol monostearate (available from Lonza under the tradename Aldo® PGHMS; DDA CO3—didecyldimethylammonium carbonate (50% solution in water/propylene glycol, prepared in accordance with U.S. Pat. Nos. 5,438,034, issued Aug. 1, 1995, and 5,523,487, issued Jun. 4, 1996); DDAC—didecyldimethylammonium chloride (80% solution in water/ethanol, Bardac® 2280, Lonza Inc.); DT95—ditallowamidoethylpolyoxyethylenemethylammonium methosulfate (70% active material, Carsosoft® DT-95); BX18—octadecyldimethylamine oxide (25% paste in water, Barlox® 18, Lonza Inc.); BX16—hexadecyldimethylamine oxide (30% solution in water, Barlox® 16, Lonza Inc.); ODAA—octadecyl acetoacetate (100% pure solid, Lonza AG); Pond.—ponderosa pine (end grain wafers of ¼×¾× 5"); SYP—southern yellow pine (end grain wafers of ¼×¾× 3½").

FIGS. 8 and 9 are results achieved with southern yellow pine, while FIGS. 1–7 are results achieved with ponderosa pine.

SUMMARY OF THE INVENTION

The present invention involves a waterproofer wood preservation system comprising a waterproofing-enhancing amount of a waterproofer composition and a biocidally-effective amount of a biocide where the waterproofer is selected from the group consisting of an alkyl dimethyl amine oxide, an alkyl acetoacetate, and a waterproofing quaternary ammonium compound, and the biocide comprises at least one biocidal quaternary ammonium compound. The waterproofer and biocidal components are mixed in a ratio ranging from 0.25:1 to 2:1 range, preferably at a ratio of 1:1.

This invention also contemplates a method for waterproofing, preserving, or waterproofing and preserving a wood substrate comprising treating said substrate with a waterproofer wood preservative system as described above. The waterproofing systems described exhibit enhanced resistance to leaching, thus substantially increasing the duration of effective protection of the treated wood.

DETAILED DESCRIPTION OF THE INVENTION

I. Waterproofers

A first type of waterproofer which is contemplated for the systems of the present invention are alkyl amine oxides. These amine oxides have the general formula wherein $R^7$ contains from 8 to 40 carbon atoms and is saturated or unsaturated. $R^8$ and $R^9$ may be methyl, ethyl, propyl, isopropyl, hydroxyethyl, hydroxyethoxyethyl or hydroxyethyl polyethoxyethyl radicals where the oxygen is linked to nitrogen by a coordinate covalent bond. If desired, $R^8$ and $R^9$ may be linked to form a cyclic group. While all of the listed amine oxides have waterproofing function, those with greater than 14 carbons in its alkyl group are particularly effective.

Special mention is made of (A) octadecyldimethylamine oxide, where $R^7$ is 18 and $R^8$ and $R^9$ are methyl, and (B) hexadecyldimethylamine oxide, where $R^7$ is 16 and $R^8$ and $R^9$ are methyl.

A second type of waterproofer contemplated for use in the present invention comprises waterproofing quaternary ammonium compounds having the formula:

wherein $R^{11}$ is a $C_{12}$–$C_{30}$ alkyl or $C_6$–$C_{20}$ aryl-substituted alkyl, and $R^{12}$ is a $C_{12}$–$C_{20}$ alkyl. Preferably, in a waterproofing quaternary ammonium compound, $R^{11}$ is a $C_{12}$–$C_{30}$ alkyl, and $R^{12}$ is a $C_{12}$–$C_{30}$ alkyl group. X may be a halide, including chloride, bromide, fluoride, iodide, or a carbonate, methosulfate, ethosulfate, acetate, propionate, hydroxide, ethylhexanoate or any other counteranion disclosed in U.S. Pat. Nos. 5,399,762 or 5,559,155.

Thus, the total number of carbon atoms is $R^{11}+R^{12} \geq 24$. More preferably, $R^{11}$ is a $C_{12}$–$C_{18}$ alkyl group, and $R^{12}$ is a $C_{12}$–$C_{18}$ alkyl group. Two preferred waterproofing quaternary ammonium compounds are di($C_{12}$ to $C_{18}$) dimethylammonium chloride and ditallowamidoethyl polyoxyethylenemethylammonium methosulfate.

A final type of waterproofer contemplated for use in the present invention comprises alkyl acetoacetates having the formula:

wherein $R^{10}$ is an alkyl group containing 8 to 40 carbon atoms, though preferably 12 to 20 carbon atoms, and is saturated or unsaturated. $R^{10}$ is $C_{18}$ in a preferred alkyl acetoacetate.

Special mention is made of octadecyl acetoacetate available from Lonza AG.

Also contemplated by the present invention are combinations of any of the above with each other, with esters or with small amounts of low molecular weight polyolefins or other waxes or resins.

These waterproofers hinder migration of the quat molecules from a substrate under wet conditions. Furthermore, where surface corrosion problems are related to the water holding properties of the quat, the waterproofer displaces or prevents the entry of water.

II. Biocides

Quaternary ammonium compounds are specifically contemplated for use as a biocide in the treatment systems of the present invention.

Biocidal quaternary ammonium compounds have the formula:

(V)

wherein $R^{11}$ is a $C_1$–$C_{20}$ alkyl or $C_6$–$C_{20}$ aryl-substituted alkyl group, $R^{12}$ is a $C_6$–$C_{20}$ alkyl group. X may be a halide, including chloride, bromide, fluoride, iodide, or a carbonate, borate, carboxylate, methosulfate, ethosulfate, acetate, propionate, hydroxide, ethylhexanoate or any other counteranion disclosed in U.S. Pat. Nos. 5,399,762 or 5,559,155. An example is didecyldimethylammonium chloride. Another example is didecyldimethylammonium carbonate.

Quaternary ammonium compounds which have biocidal properties include those where $R^{11}$ is a $C_6$–$C_{18}$ alkyl or a benzyl group, and $R^{12}$ is a $C_6$–$C_{18}$ alkyl group. Thus, the total number of carbons is $R^{11}+R^{12}=16$–24. Preferably, $R^{11}$ is a $C_8$–$C_{12}$ alkyl group, and $R^{12}$ is a $C_8$–$C_{12}$ alkyl group. When $R^{11}$ is benzyl, $R^{12}$ is preferably $C_{12}$–$C_{16}$ alkyl group.

Special mention is made of quats wherein $R^{11}$ is a $C_8$ alkyl, $C_9$ isoalkyl, $C_{10}$ alkyl, $C_{12}$ alkyl, or benzyl group; and $R^{12}$ is a $C_{10}$ alkyl, $C_{12}$, $C_{14}$ alkyl or $C_{16}$ alkyl group. A preferred chloride quat is didecyldimethylammonium chloride wherein $R^{11}$ and $R^{12}$ are a n-$C_{10}$ group. This quat may be usefully applied in the form of an 80% water/ethanol solution (Bardac® 2280; Lonza Inc.).

Useful carbonate quats have the above-shown formula wherein $R^{11}$ is a methyl, $C_8$ alkyl, $C_9$ isoalkyl, $C_{10}$ alkyl, $C_{12}$ alkyl, $C_{14}$ alkyl, $C_{16}$ alkyl, or benzyl group; and $R^{12}$ is a $C_{10}$ alkyl, $C_{12}$ alkyl, $C_{14}$ alkyl, or $C_{16}$ alkyl group.

A preferred carbonate quat is didecyldimethylammonium carbonate wherein $R^{11}$ and $R^{12}$ are a n-$C_{10}$ alkyl group. Didecyldimethylammonium carbonate, as a 70–80 percent (by weight) solution, is a yellow/orange liquid that has a slightly fruity odor. This formulation has a flash point of about 160° F., and reacts with carboxyl containing compounds. This carbonate quat is made by the method disclosed in U.S. Pat. Nos. 5,523,487 and 5,438,034.

One or more of the carbonate quats alone or in combination with the corresponding chloride quat can be formulated in the present waterproofer wood preservative systems.

The two principle components of the present waterproofer and preservative system, the waterproofer and the biocide, should be combined in amounts which allow the waterproofer to prevent exposure of the treated wood to water and the biocide to function against biological attack, such as fungal growth. In general, a ratio of waterproofer to biocide of 1:1 has been found effective, with a range of 0.25:1 to 1:0.25 anticipated to be within the functional range. The concentration of waterproofer found effective is 0.25–4 wt %, more particularly, 0.5–2 wt %. The concentration of biocide found effective is 0.25–4 wt %, more particularly, 0.5–2 wt %.

DESCRIPTION OF THE PREFERRED EMBODIMENTS

The following examples illustrate the invention without limitation. All parts and percentages are given by weight unless otherwise indicated.

Treating solutions were prepared by mixing the appropriate weight of the waterproofer and quaternary ammonium compound, warning on a hot water bath to melt/dissolve the components into each other and then diluting with warm (40–50 C) water with good stirring.

Wood Treatment

The wood treated was either Ponderosa Pine or Southern Yellow Pine (SYP) end-grain wafers. The dimensions of the ponderosa pine pieces are 5"×0.75"×0.25" and the SYP are 3.5"×0.75"×0.25". The specimen were equilibrated at ambient conditions before treating and were weighed. The samples were then placed in a vacuum desiccator equipped with an addition funnel and evacuated to a pressure (vacuum) of 0.1 atmosphere for 15 minutes. The treating solution was added to the sample and the pressure in the desiccator increased to atmospheric. The samples were allowed to remain in the solution for five minutes, then removed, blotted, and allowed to air dry to constant weight. The control TWS material, which is available in mineral spirits, was applied to samples via a simple one minute soak procedure.

Soaking experiments were carried out by immersing weighed measured samples in deionized water for 30 minutes. The samples were removed, surface water was blotted and the samples were weighed and the weight percent of water absorbed was calculated for each sample.

After the swelling experiment, the samples were air dried and then placed outside on a flat piece of plywood for exposure to the weather. Periodically, the samples were returned to the laboratory, air dried to constant weight and once again soaked for 30 minutes and the water uptake determined. Water uptake for the last measurement available is given in the tables. Data are reported in several tables. Since wood can vary, care was taken to use only matched specimens in each table grouping.

Waterproofing Calculations

Waterproofing ability is judged by the amount of water that is absorbed by a wooden specimen on immersion for a give time in water. Waterproofing index numbers (WR Index) were calculated by comparing a treated sample with a matched untreated control specimen using the following equation:

$$\text{WR Index} = \frac{[\% \text{ Uptake Untreated Control} - \% \text{ Uptake Treated Sample}]}{\% \text{ Uptake Untreated Control}} \times 100$$

Any positive index number indicates a degree of waterproofing for the composition. Higher numbers are better than low numbers. A formulation that totally prevents water absorption would have a rating of 100. For certain millwork applications, an index of 60 is required. Any positive number indicates some degree of waterproofing while higher numbers signify the best materials. Index numbers of 60 or higher signify particularly good waterproofers. By this criterion, all of the identified materials are good waterproofers. The waterproofing properties are compared to both a non-biocidal waterproofer, Thompson's Waterseal®, available in mineral spirits in the over-the-counter marketplace and a quat combination with PGHMS which is the subject of U.S. Ser. No. 08/074,314.

RESULTS OF EXPERIMENTS

Figure 1:
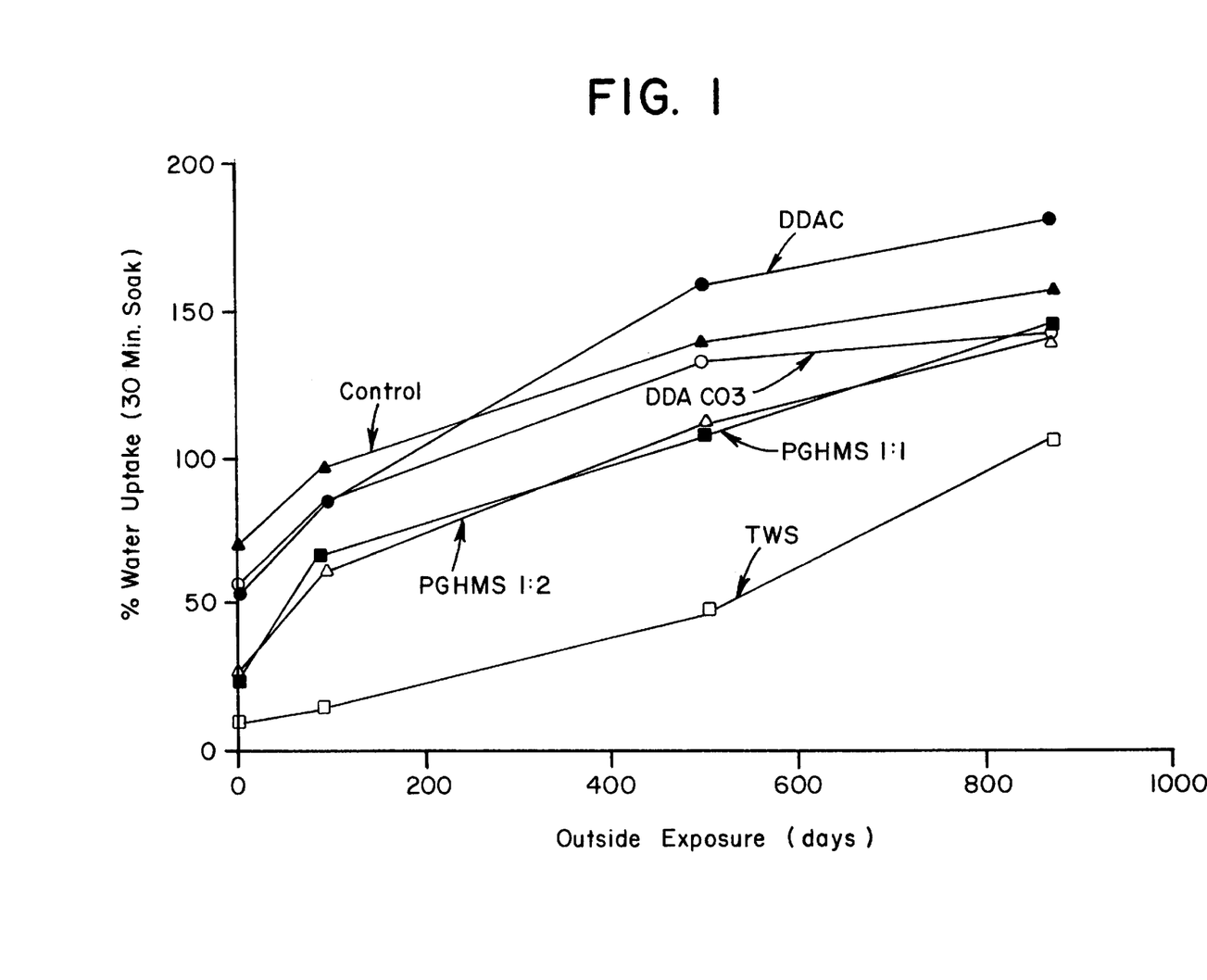
FIG. 1 is a graphic representation of the data of Table 1, documenting the results over time for the waterproofing ability of quats and quats with PGHMS, and the TWS control.
Figure 2:
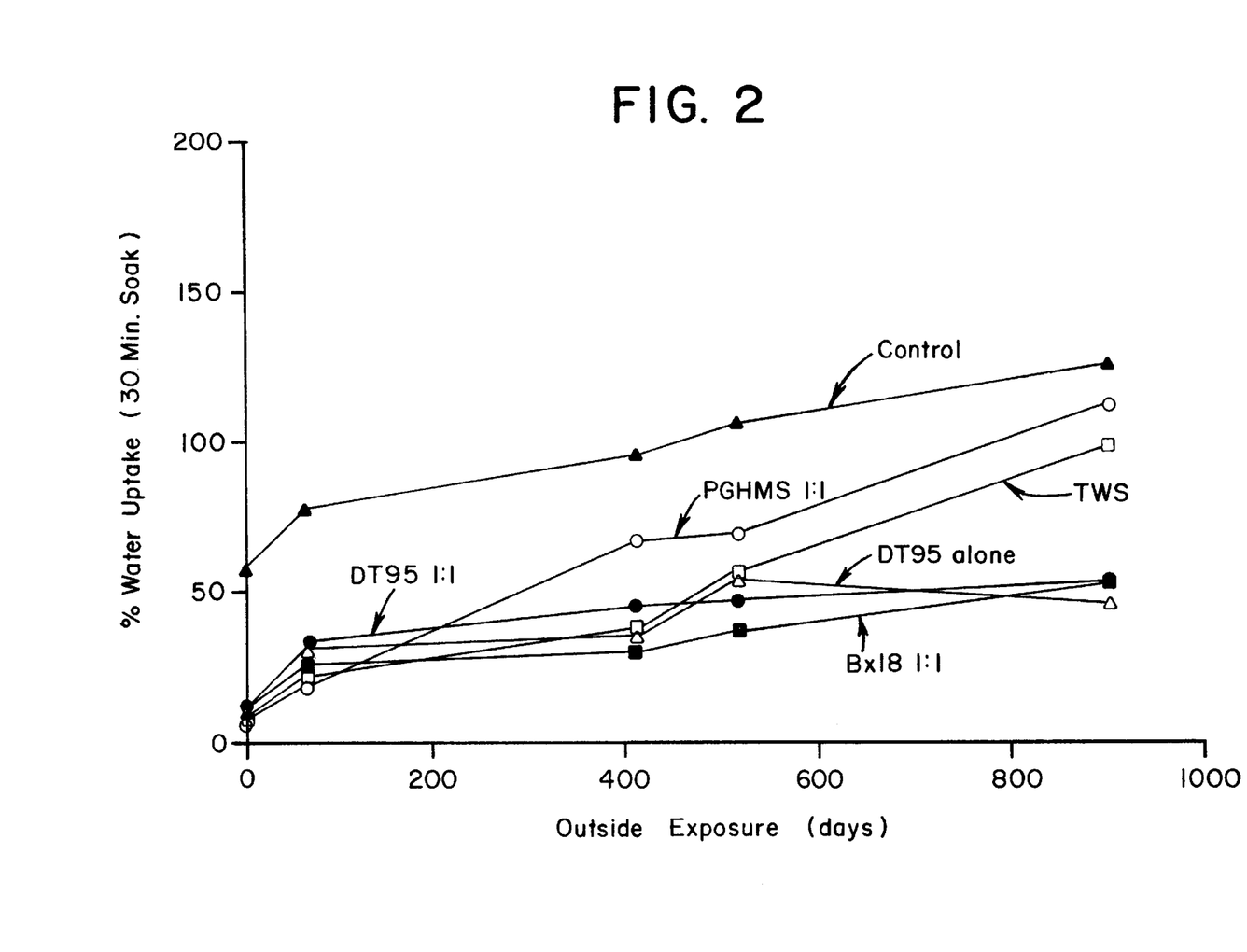
FIG. 2 is a graphic representation of the data of Table 2, showing the results achieved over time by mixing the quat with the waterproofing composition.
Figure 3:
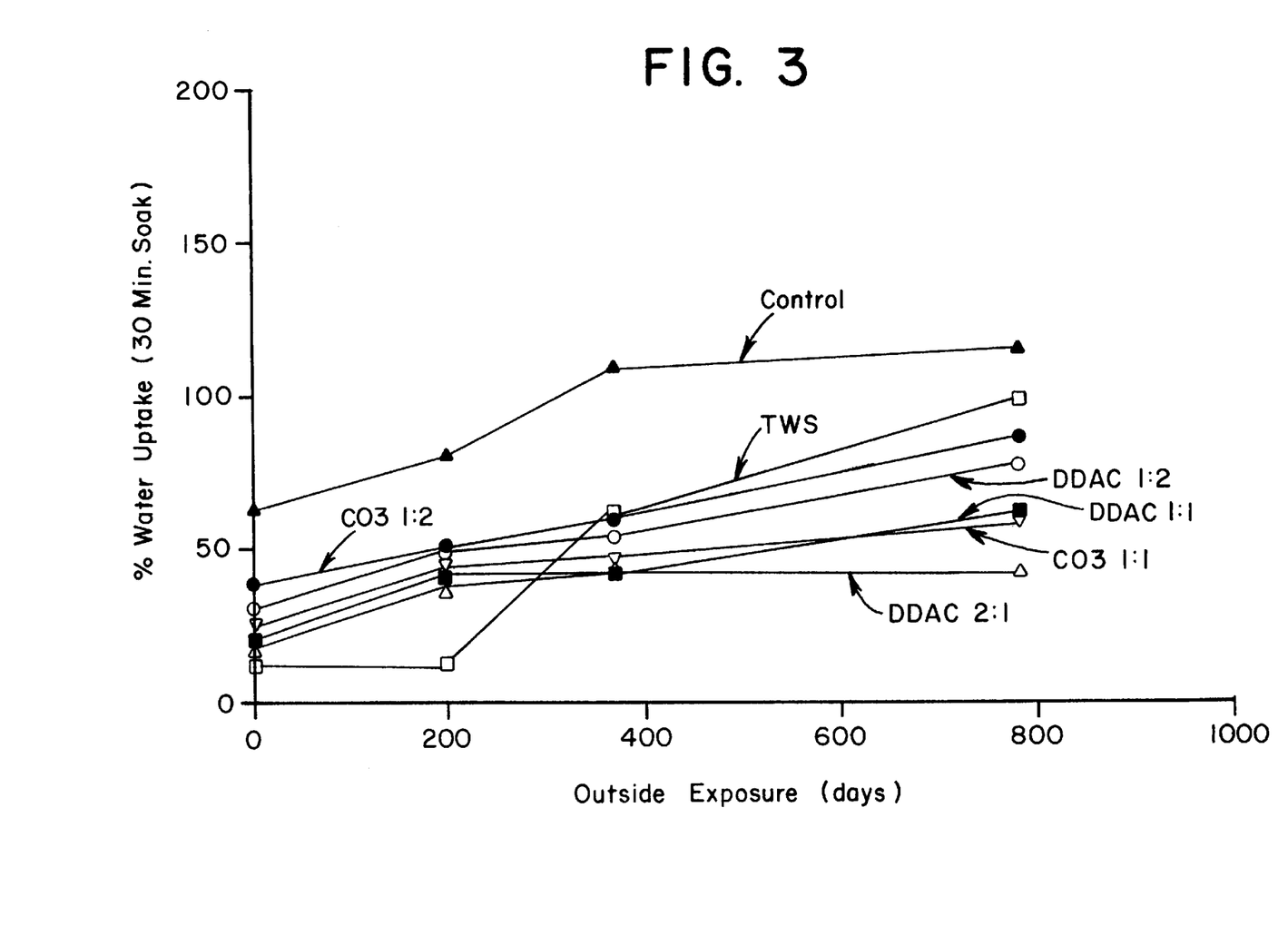
FIG. 3 is a graphic representation of the data of Table 3, showing the function of DDAC and DDA CO3 in combination with the waterproofers.
Figure 4:
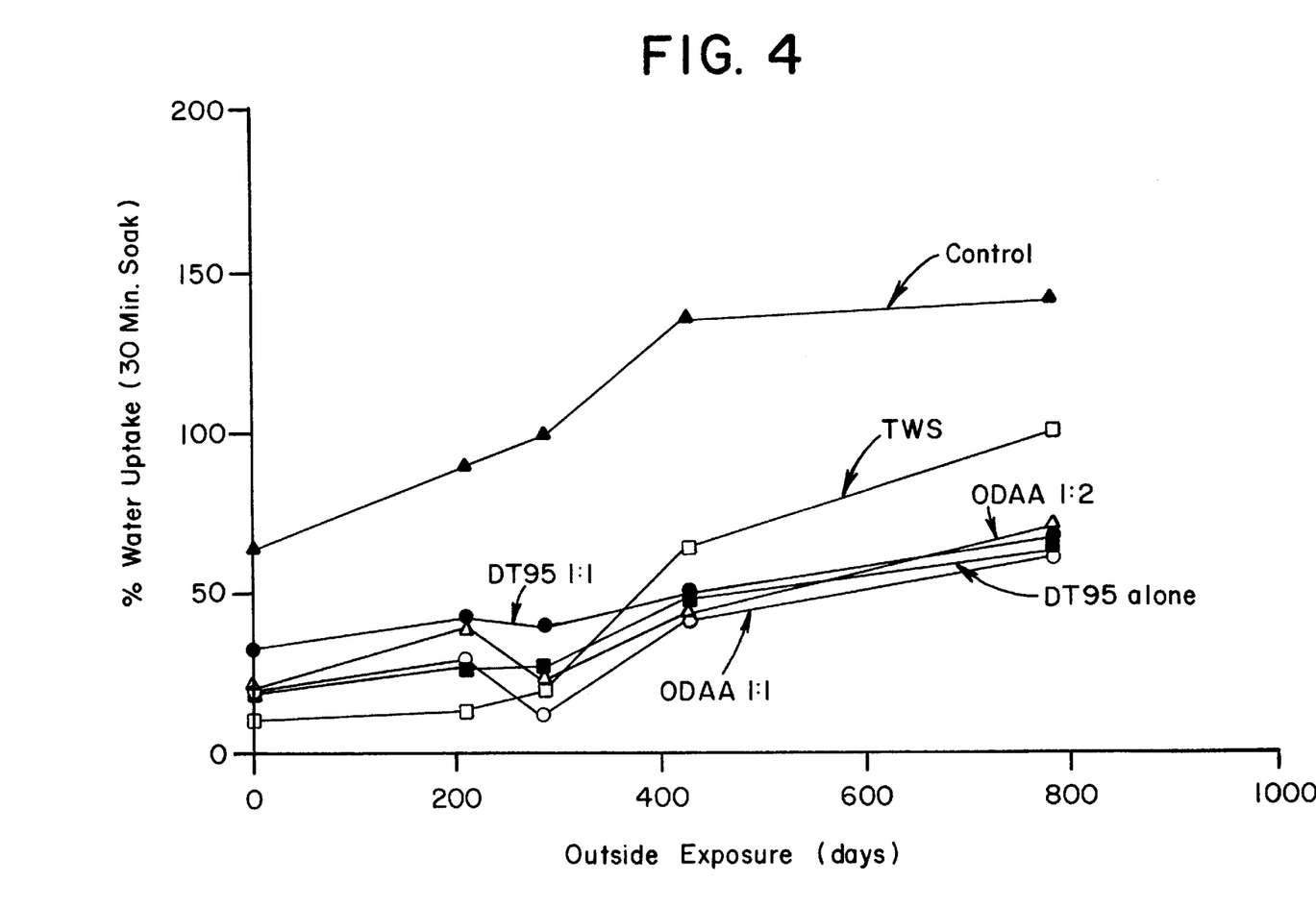
FIG. 4 is a graphic representation of the data of Table 4, documenting the retention of waterproofing abilities of the combination waterproofing system.
Figure 5:
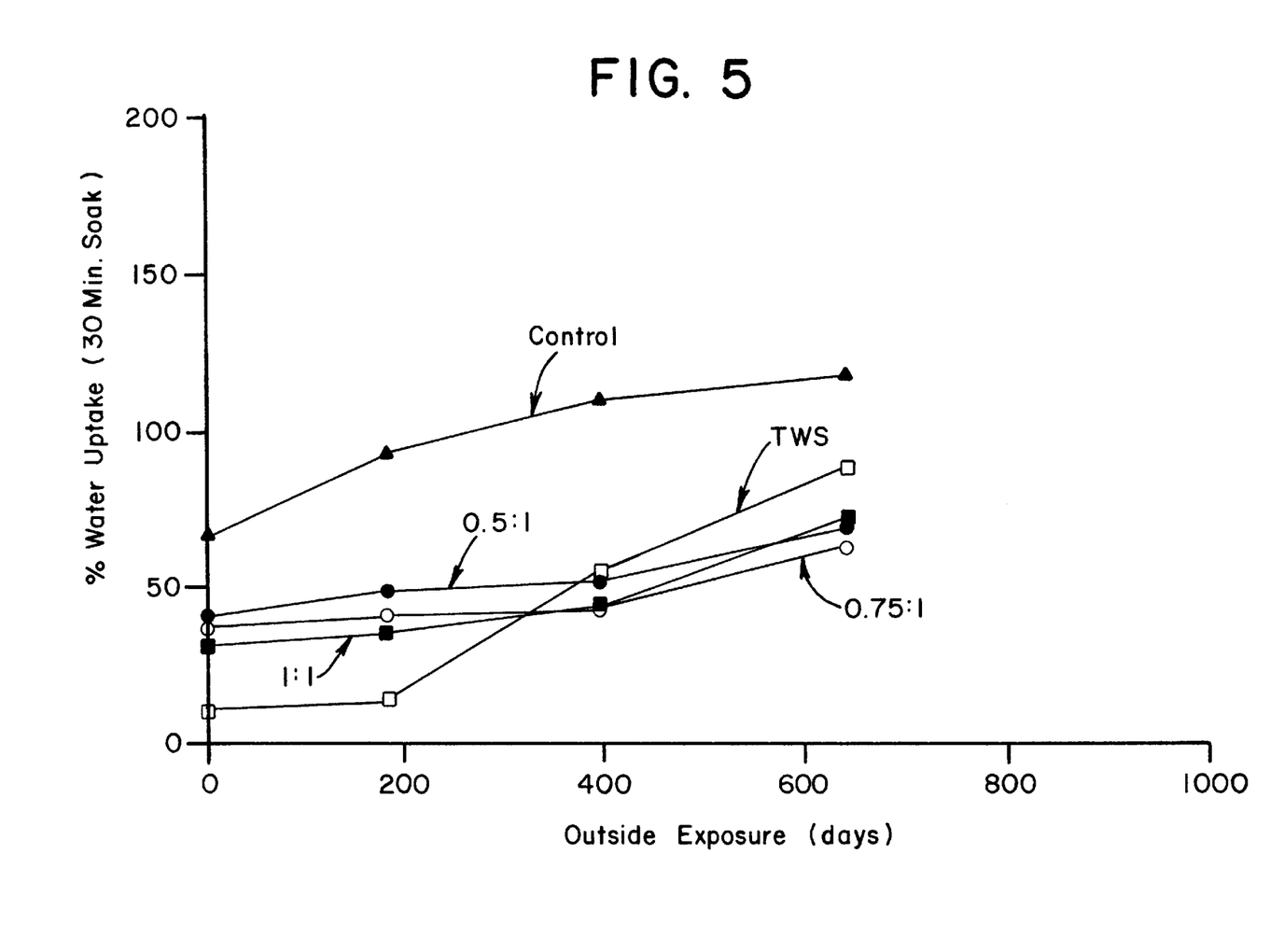
FIG. 5 is a graphic representation of the data of Table 5, showing the function of Carsoquat® 868 in combination with quat as a waterproofing system.
Figure 6:
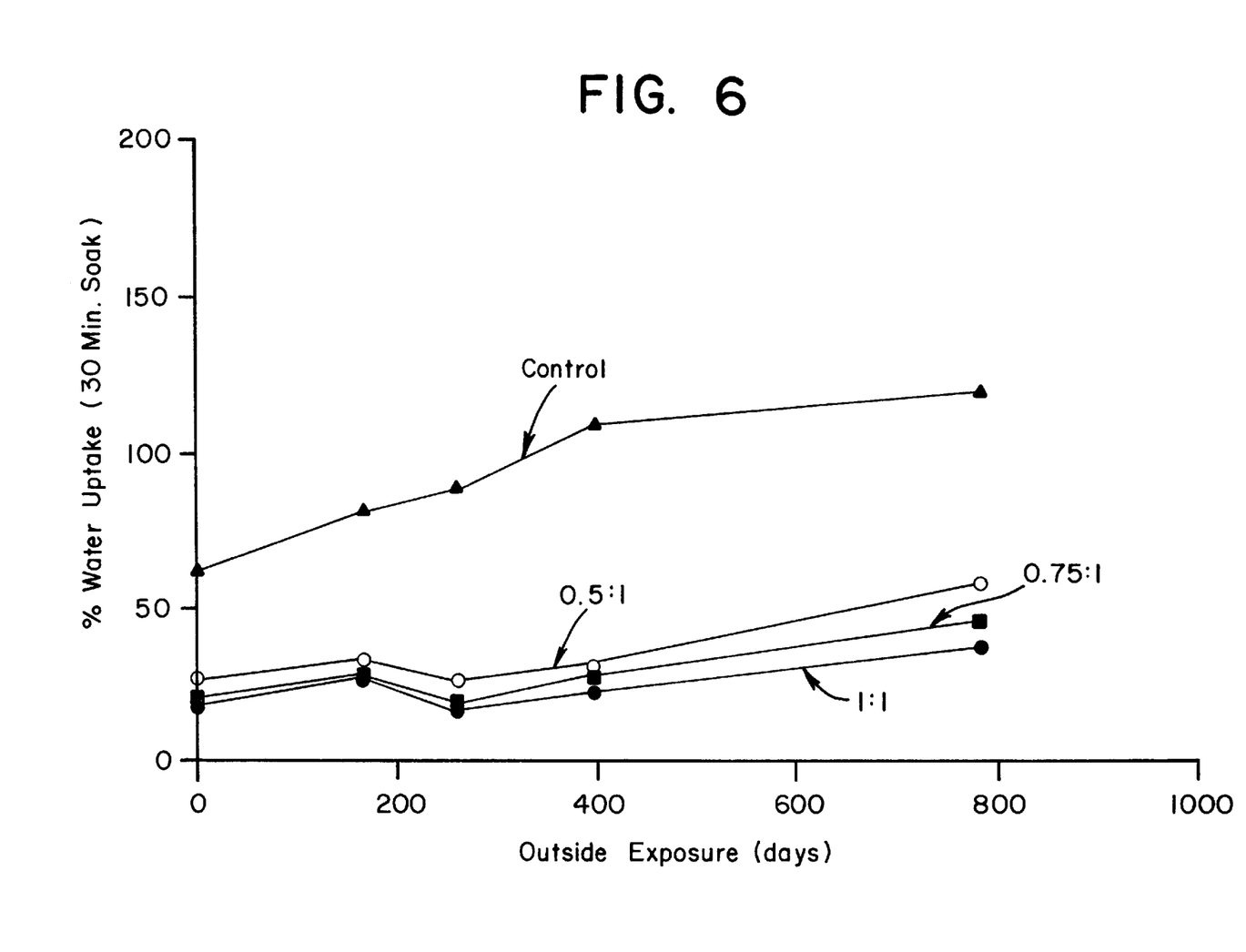
FIG. 6 is a graphic representation of the data of Table 6, demonstrating the function of Barlox® 18 with DDA CO3 as a waterproofing system.
Figure 7:
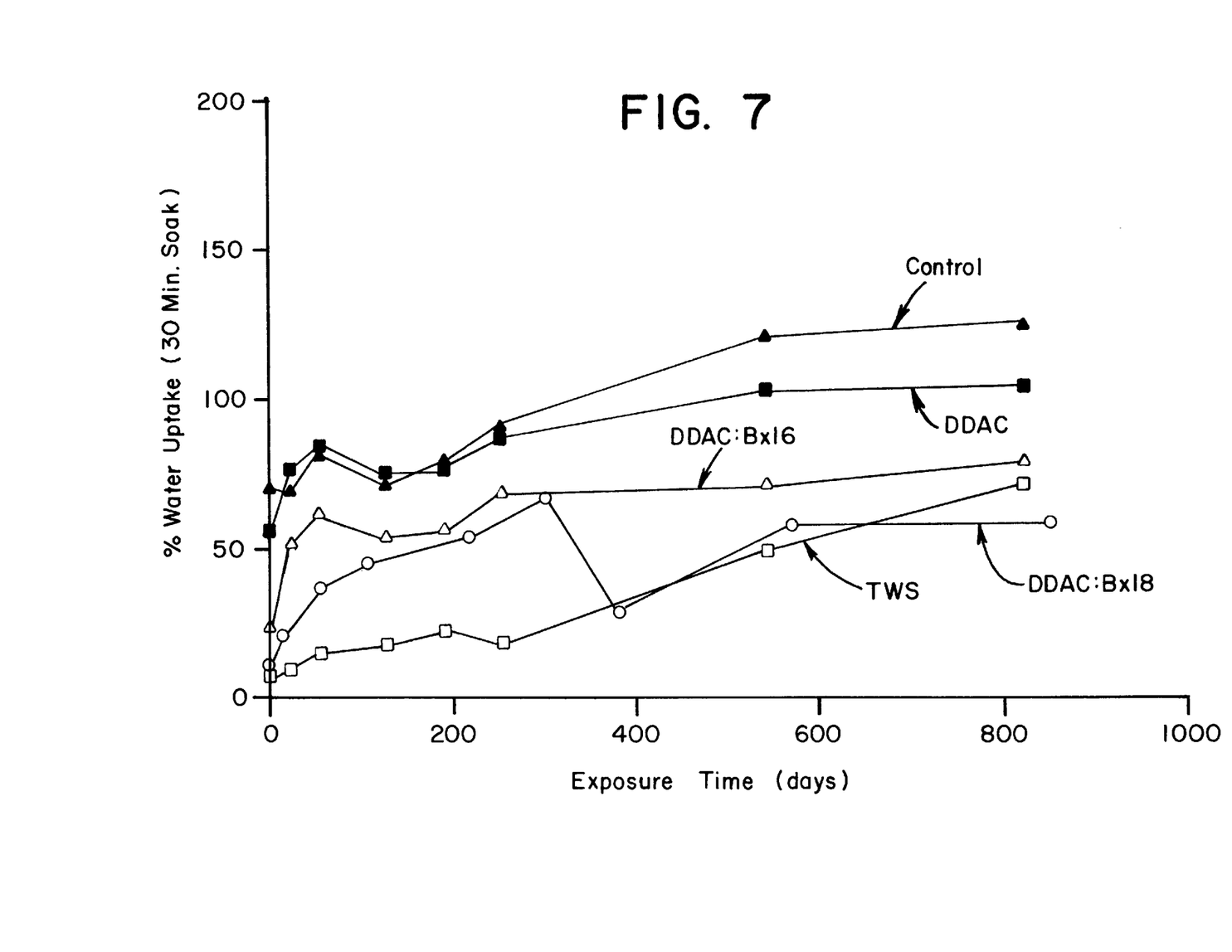
FIG. 7 is a graphic representation of the data of Table 7, providing a comparison of the function of BX18 with that of BX16 in combination with DDAC.
Figure 8:
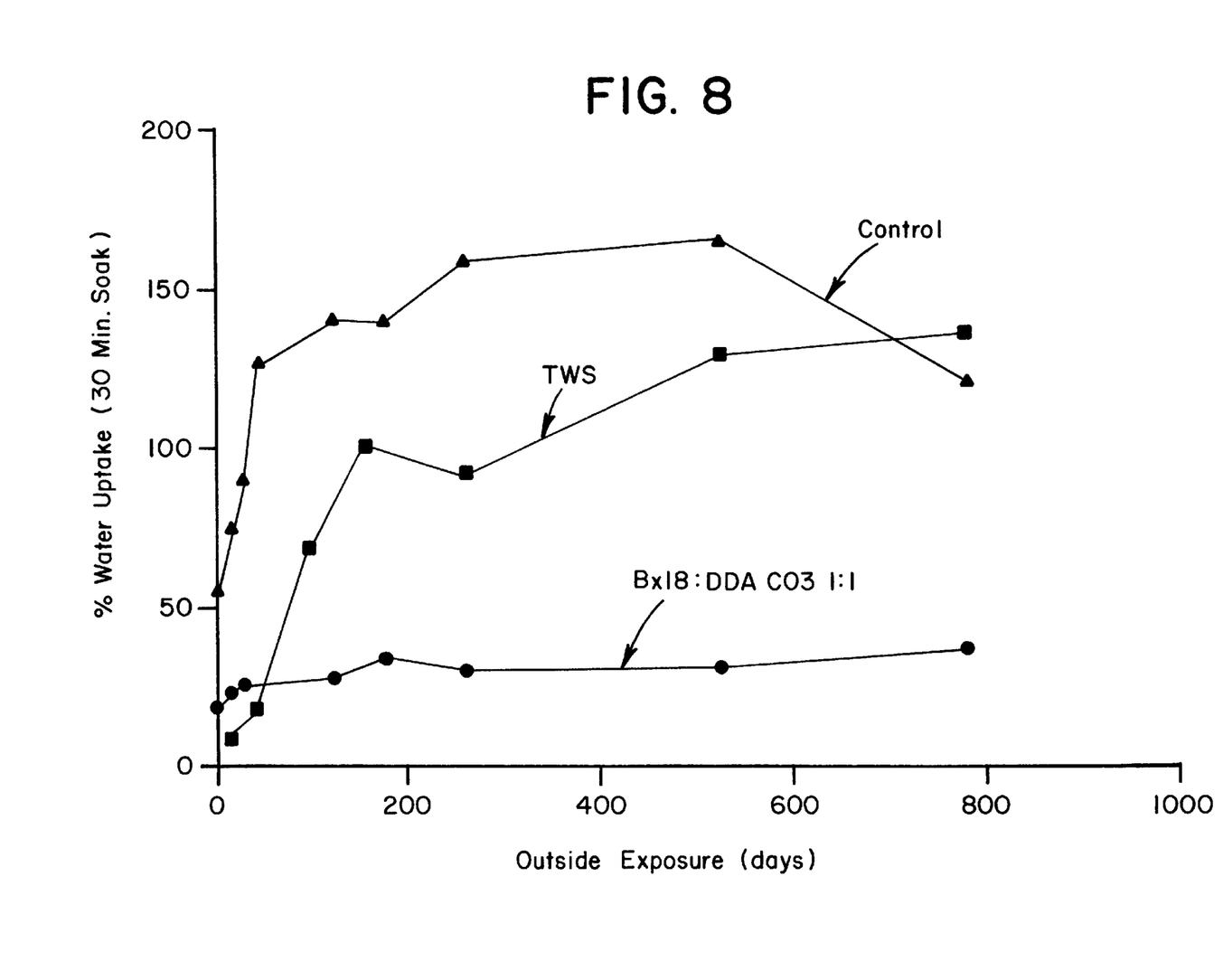
FIG. 8 is a graphic representation of the data of Table 8.
Figure 9:
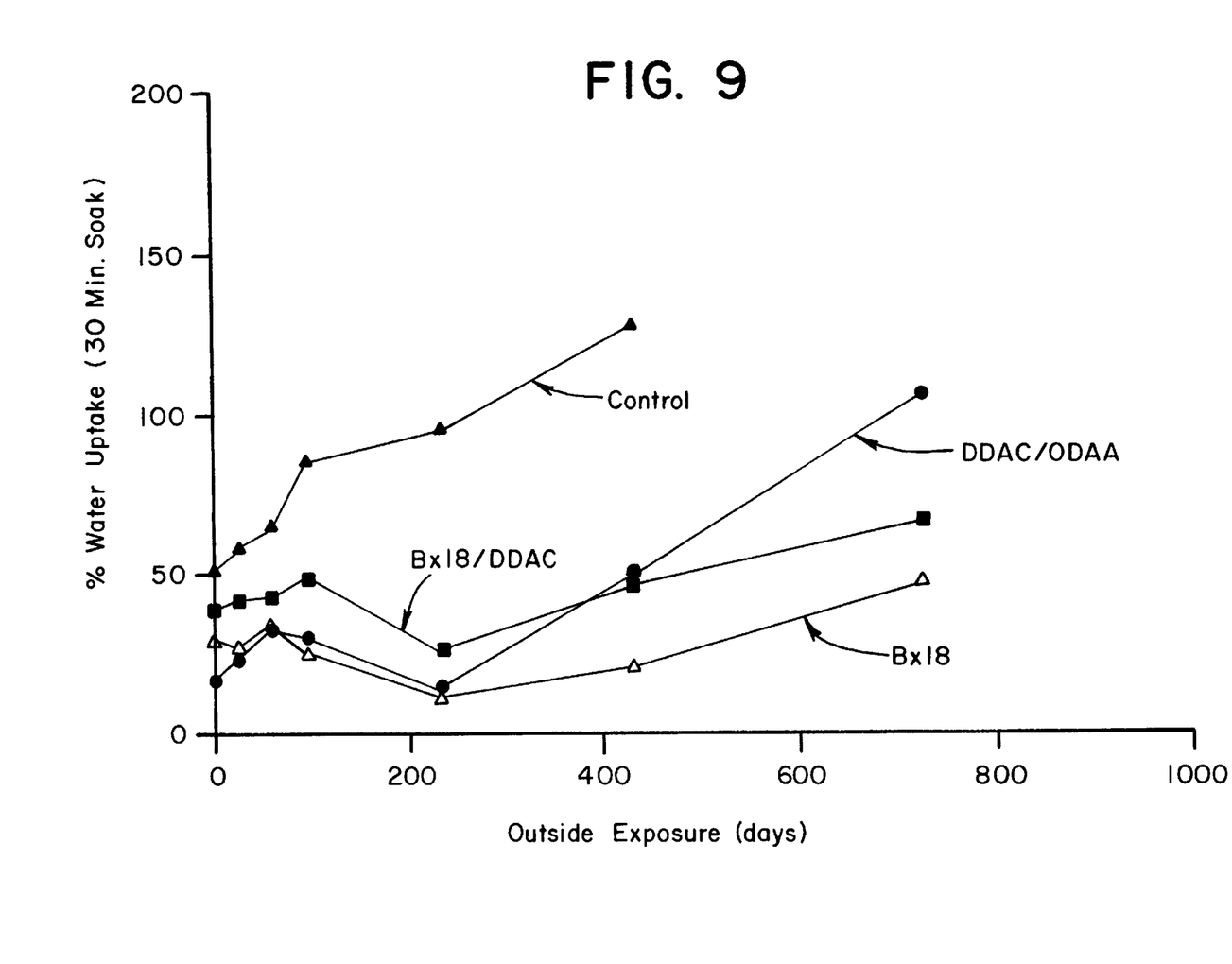
FIG. 9 is a graphic representation of the data of Table 9.

Data are collected in nine tables and figures. For each table, columns give the name of the waterproofer (WR), the name of the biocide or quat (B), the amount of each in component in percent, the water uptake of initially treated samples after 30 minutes soaking, the calculated waterproofing index number (WR Index), and the percent uptake after weathering for a given time. Figures corresponding to the data in the Tables are also included (see FIGS. 1–9) showing the percent water uptake (for thirty minute soaks) as a function of the number of days of weathering.

For each series of samples (represented by a given table), a matched set of end-faced wood samples were used. The control in each series is used as the basis for experimental result calculations in that series.

In general, the results demonstrate that while prior art compounds such as TWS are initially as effective as the combinations of this application, only the presently taught wood preservation systems are effective over long periods of weathering. Thus, as evident in the Tables which follow, TWS, DT95, PGHMS and BX18 with DDA CO3 all show similar waterproofing properties at the early measurement times, but after three years, wood treated with TWS or PGHMS+DDA CO3 have similar profiles to the untreated control, whereas the new combinations disclosed here performed well after three years.

TABLE I

Ponderosa Pine Treated Controls with DDA CO3 DT95

| WR | B | WR:B | % Uptake Start | WR Index | % Uptake 870 days |
|---|---|---|---|---|---|
| Control | NONE | | 70 | 0 | 158 |
| TWS | NONE | | 9 | 87 | 107 |
| | DDA CO3 | 0:1 | 56 | 20 | 143 |
| | DDAC | 0:1 | 53 | 24 | 182 |
| PGMHS | DDA CO3 | 1:2 | 26 | 63 | 142 |
| PGMHS | DDA CO3 | 1:1 | 24 | 66 | 146 |

These data indicate that quats alone are not good waterproofers and any function which they have is quickly lost over time. Further, combining PGMHS and DDA CO3 helps initially to retain the waterproofing function.

TABLE II

Ponderosa Pine Treated with DDA CO3 and BX18 and DT95

| WR | B | WR:B | % Uptake Start | WR Index | % Uptake 900 days |
|---|---|---|---|---|---|
| Control | | | 56 | 0 | 125 |
| TWS | | | 8 | 86 | 98 |
| BX18 | DDA CO3 | 1:1 | 12 | 78 | 52 |
| PGHMS | DDA CO3 | 1:1 | 9 | 84 | 112 |
| DT 95 | NONE | | 10 | 82 | 46 |
| DT 95 | DDA CO3 | 1:1 | 11 | 80 | 53 |

These data indicate that BX18 and DT 95 are both effective in combination with the quat, and show significant retention of the waterproofing qualities over time. Surprisingly, the systems combining DDA CO3 with BX18 or DT 95 retain waterproofing ability significantly longer than TWS or PGHMS combined with DDA CO3.

TABLE III

Ponderosa Pine Treated with DDAC and DDA CO3 and DT95

| WR | B | WR:B | % Uptake Start | WR Index | % Uptake 780 days |
|---|---|---|---|---|---|
| Control | | | 63 | 0 | 116 |
| TWS | | | 12 | 81 | 99 |
| DT 95 | DDAC | 0.5:1 | 31 | 51 | 78 |
| DT 95 | DDAC | 1:1 | 21 | 67 | 61 |
| DT 95 | DDAC | 2:1 | 20 | 68 | 42 |
| DT 95 | DDA CO3 | 0.5:1 | 38 | 40 | 87 |
| DT 95 | DDA CO3 | 1:1 | 24 | 62 | 57 |

These data indicate that both DDAC and DDA CO3 are effective in combination with DT 95, particularly after long weathering times.

TABLE IV

Ponderosa Pine Treated with DDA CO3 and ODAA, DT 95

| WR | B | WR:B | % Uptake Start | WR Index | % Uptake 780 days |
|---|---|---|---|---|---|
| Control | | | 64 | 0 | 142 |
| TWS | | | 10 | 84 | 100 |
| ODAA | DDA CO3 | 0.5:1 | 19 | 70 | 70 |
| ODAA | DDA CO3 | 1:1 | 19 | 70 | 61 |
| DT 95 | DDA CO3 | 1:1 | 32 | 50 | 67 |
| DT 95 | NONE | 1:0 | 18 | 72 | 62 |

These data indicate that a 1:1 ratio between waterproofer and biocide is effective.

TABLE V

Ponderosa Pine with DDAC and 868

| WR | B | WR:B | % Uptake Start | WR Index | % Uptake 640 days |
|---|---|---|---|---|---|
| Control | | | 65 | 0 | 118 |
| TWS | | | 11 | 83 | 88 |
| 868 | DDAC | 0.5:1 | 39 | 40 | 69 |
| 868 | DDAC | 0.75:1 | 36 | 45 | 63 |
| 868 | DDAC | 1:1 | 30 | 54 | 71 |

These data show that 868 is an effective waterproofer in combination with DDAC and shows excellent retention of properties over time.

TABLE VI

Ponderosa Pine Treated with DDA CO3 and BX18

| WR | B | WR:B | % Uptake Start | WR Index | % Uptake 780 days |
|---|---|---|---|---|---|
| Control | | | 59 | 0 | 120 |
| BX18 | DDA CO3 | 0.5:1 | 28 | 53 | 58 |
| BX18 | DDA CO3 | 0.75:1 | 20 | 66 | 45 |
| BX18 | DDA CO3 | 1:1 | 19 | 68 | 37 |

These data show that BX18 is an effective waterproofer over a range of WR:B ratios shown.

TABLE VII

Ponderosa Pine Treated with DDAC and BX18 and BX16

| WR | B | WR:B | % Uptake Start | WR Index | % Uptake 540 days |
|---|---|---|---|---|---|
| Control | | | 70 | 0.00 | 121 |
| TWS | | | 7 | 90 | 49 |
| NONE | DDAC | 0:1 | 52 | 26 | 103 |
| BX16 | DDAC | 1:1 | 22 | 69 | 71 |
| BX18 | DDAC | 1:1 | 11 | 84 | 58 |

These data indicate that the $C_{16}$ and the $C_{18}$ compounds are both effective.

TABLE VIII

Southern Yellow Pine Treated with DDA CO3 and BX18

| WR | B | WR:B | % Uptake Start | WR Index | % Uptake 780 days |
|---|---|---|---|---|---|
| Control | | | 54 | 0 | 121 |
| TWS | | | 9 | 83 | 136 |
| BX18 | DDA CO3 | 1:1 | 18 | 67 | 37 |

These data indicate that good results can be achieved with BX18 on both Southern Yellow, as well as Ponderosa pine. Again, the data in Table VIII highlight the long term effectiveness of the waterproofer system of the invention.

TABLE IX

Southern Yellow Pine Treated with DDAC and BX18, ODAA

| WR | B | WR:B | % Uptake Start | WR Index | % Uptake 725 days |
|---|---|---|---|---|---|
| Control | | | 51 | 0 | 128 |
| BX18 | NONE | 1:0 | 30 | 41 | 47 |
| BX18 | DDAC | 1:1 | 38 | 25 | 67 |
| ODAA | DDAC | 1:1 | 17 | 67 | 106 |

This data show ODAA together with DDAC is also effective on Southern Yellow Pine.

What is claimed is:

1. A waterproofing wood preservative system comprising a waterproofer selected from the group consisting of an alkyl amine oxide, an alkyl acetoacetate, and a waterproofing quaternary ammonium compound and a biocide comprising at least one biocidal quaternary ammonium compound wherein said waterproofing quaternary ammonium compound is a $C_{12}-C_{30}$ alkyl or $C_6-C_{20}$ aryl-substituted alkyl, $C_{12}-C_{30}$ alkyl quaternary ammonium composition and said biocidal quaternary ammonium compound is a $C_8-C_{12}$ alkyl or $C_6-C_{20}$ aryl-substituted alkyl, $C_8-C_{10}$ alkyl quaternary ammonium composition.

2. The waterproofing wood preservative system of claim 1 wherein said alkyl amine oxide has the formula:

wherein $R^7$ is $C_8$ to $C_{40}$ and is saturated or unsaturated;

$R^8$ and $R^9$ are independently selected from the group consisting of methyl, ethyl, propyl, isopropyl, hydroxyethyl, hydroxyethoxyethyl and hydroxyethyl polyethoxyethyl; or $R^8$ and $R^9$ are combined to form a cyclic group.

3. The waterproofing wood preservative system of claim 2 wherein $R^7$ is $C_{18}$ and $R^8$ and $R^9$ are methyl.

4. The waterproofing wood preservative system of claim 2 wherein wherein $R^7$ is $C_{16}$ and $R^8$ and $R^9$ are methyl.

5. The waterproofing wood preservative system of claim 1 wherein said alkyl acetoacetate has the formula:

wherein $R^{10}$ is a $C_8-C_{40}$ alkyl and is saturated or unsaturated.

6. The waterproofing wood preservative system of claim 5 wherein $R^{10}$ is $C_{18}$.

7. The waterproofing wood preservative system of claim 1 wherein the waterproofing quaternary ammonium compound is di($C_{12}$ to $C_{18}$)dimethylammonium chloride.

8. The waterproofing wood preservative system of claim 1 wherein the waterproofing quaternary ammonium compound is ditallowamidoethylpolyoxyethylenemethylammonium methosulfate.

9. The waterproofing wood preservative system of claim 1, wherein said biocidal quaternary ammonium composition comprises a $C_6-C_{12}$ alkyl or $C_6-C_{20}$ aryl-substituted, $C_6-C_{10}$ alkyl quaternary ammonium chloride having the formula:

wherein $R^{11}$ is a $C_6-C_{12}$ alkyl or $C_6-C_{20}$ aryl-substituted alkyl group, and $R^{12}$ is a $C_6-C_{10}$ alkyl group.

10. The waterproofing wood preservative system of claim 9 wherein $R^{11}$ and $R^{12}$ are each decyl.

11. The waterproofing wood preservative system of claim 1, wherein said biocidal quaternary ammonium composition comprises a $C_6-C_{12}$ alkyl or $C_6-C_{20}$ aryl-substituted alkyl, $C_6-C_{10}$ alkyl quaternary ammonium carbonate having the formula wherein $R^{13}$ is a $C_6$–$C_{12}$ alkyl or $C_6$–$C_{20}$ aryl-substituted alkyl group, and $R^{14}$ is a $C_6$–$C_{10}$ alkyl group.

12. The waterproofing wood preservative system of claim 11 wherein $R^{13}$ and $R^{14}$ are each decyl.

13. The waterproofing wood preservative system of claim 1, comprising from about 0.25 to about 4 parts by weight of a biocidal quaternary ammonium compound, from about 0.25 to about 4 parts by weight of a waterproofing quaternary ammonium compound, and from about 92 to about 99.5 parts by weight of solvent based upon 100 parts by weight of said biocidal and waterproofing compounds and solvent combined.

14. A method for waterproofing a wood substrate comprising treating said substrate with the waterproofing wood preservative system of claim 13.

15. A method for preserving a wood substrate comprising treating said substrate with the waterproofer wood preservative system of claim 13.

16. A method for waterproofing and preserving a wood substrate comprising treating said substrate with the waterproofer wood preservative system of claim 13.

* * * * *